United States Patent [19]

Fryer et al.

[11] 4,427,589
[45] Jan. 24, 1984

[54] PYRIMIDO[4,5-d][2]BENZAZEPINES

[75] Inventors: Rodney I. Fryer, North Caldwell; Eugene J. Trybulski, Parsippany; Armin Walser, West Caldwell, all of N.J.

[73] Assignee: Hoffmann-La Roche Inc., Nutley, N.J.

[21] Appl. No.: 286,123

[22] Filed: Jul. 23, 1981

Related U.S. Application Data

[63] Continuation-in-part of Ser. No. 175,554, Aug. 5, 1980, abandoned.

[51] Int. Cl.³ .......................................... C07D 487/04
[52] U.S. Cl. .............................. 260/243.3; 424/244; 424/250
[58] Field of Search ..................................... 260/243.3

Primary Examiner—Paul M. Coughlan, Jr.
Assistant Examiner—D. B. Springer
Attorney, Agent, or Firm—Jon S. Saxe; Bernard S. Leon; Frank P. Hoffman

[57] ABSTRACT

There is presented a compound of the formula

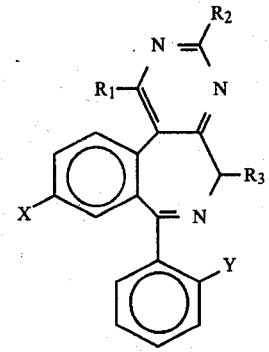

wherein
$R_1$ is selected from the group consisting of hydrogen, lower alkyl, chloro, bromo, alkoxy, hydroxy, lower alkyl substituted thio and $NR_4R_5$ wherein $R_4$ and $R_5$ are hydrogen, lower alkyl and di-substituted lower alkylamino lower alkyl;
$R_2$ is selected from the group consisting of hydrogen, lower alkyl and amino;
$R_3$ is selected from the group consisting of hydrogen, acyloxy and hydroxy;
X is halogen and Y is hydrogen or halogen and the N-oxides thereof when $R_3$ is hydrogen
and the pharmaceutically acceptable salts thereof.

The pyrimido[4,5-d][2]benzazepines are useful as anxiolytic and sedative agents.

Also presented are processes and intermediates in the production of the above pyrimido[4,5-d][2]benzazepines.

5 Claims, No Drawings

PYRIMIDO[4,5-D][2]BENZAZEPINES

RELATED APPLICATIONS

This is a continuation-in-part application of copending U.S. patent application Ser. No. 175,554, filed Aug. 5, 1980, now abandoned.

DESCRIPTION OF THE INVENTION

There is presented a compound of the formula

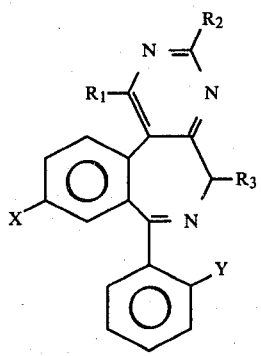

I wherein $R_1$ is selected from the group consisting of hydrogen, lower alkyl, chloro, bromo, alkoxy, hydroxy, lower alkyl substituted thio and $NR_4R_5$ wherein $R_4$ and $R_5$ are hydrogen, lower alkyl and di-substituted lower alkylamino lower alkyl;

$R_2$ is selected from the group consisting of hydrogen, lower alkyl and amino;

$R_3$ is selected from the group consisting of hydrogen, acyloxy and hydroxy;

X is halogen and Y is hydrogen or halogen and the N-oxides thereof when $R_3$ is hydrogen and the pharmaceutically acceptable salts thereof.

As used herein, the terms "halo" or "halogen" refer to the group chloro, bromo or fluoro.

By the term "lower alkyl" is meant a $C_1$ to $C_7$ hydrocarbon radical which may be straight or branched chain, such as, methyl, ethyl, propyl, isopropyl, butyl, etc.

By the term "acyloxy" is meant an organic radical derived from an organic acid by the removal of the hydrogen group, such as, acetyloxy, benzoyloxy, etc.

The following reaction schemes set forth preparative means to arrive at the novel and product of formula I:

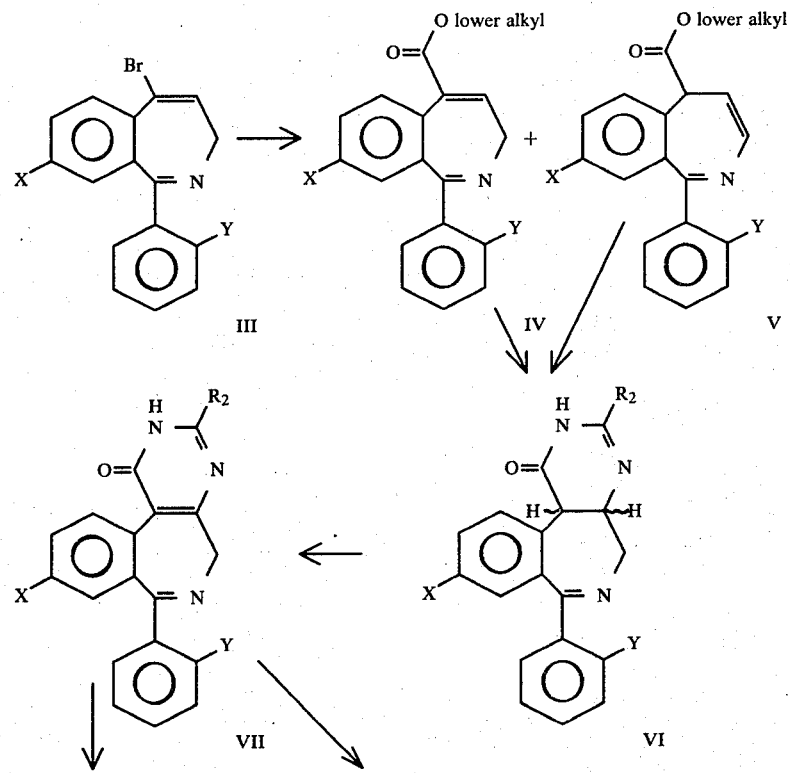

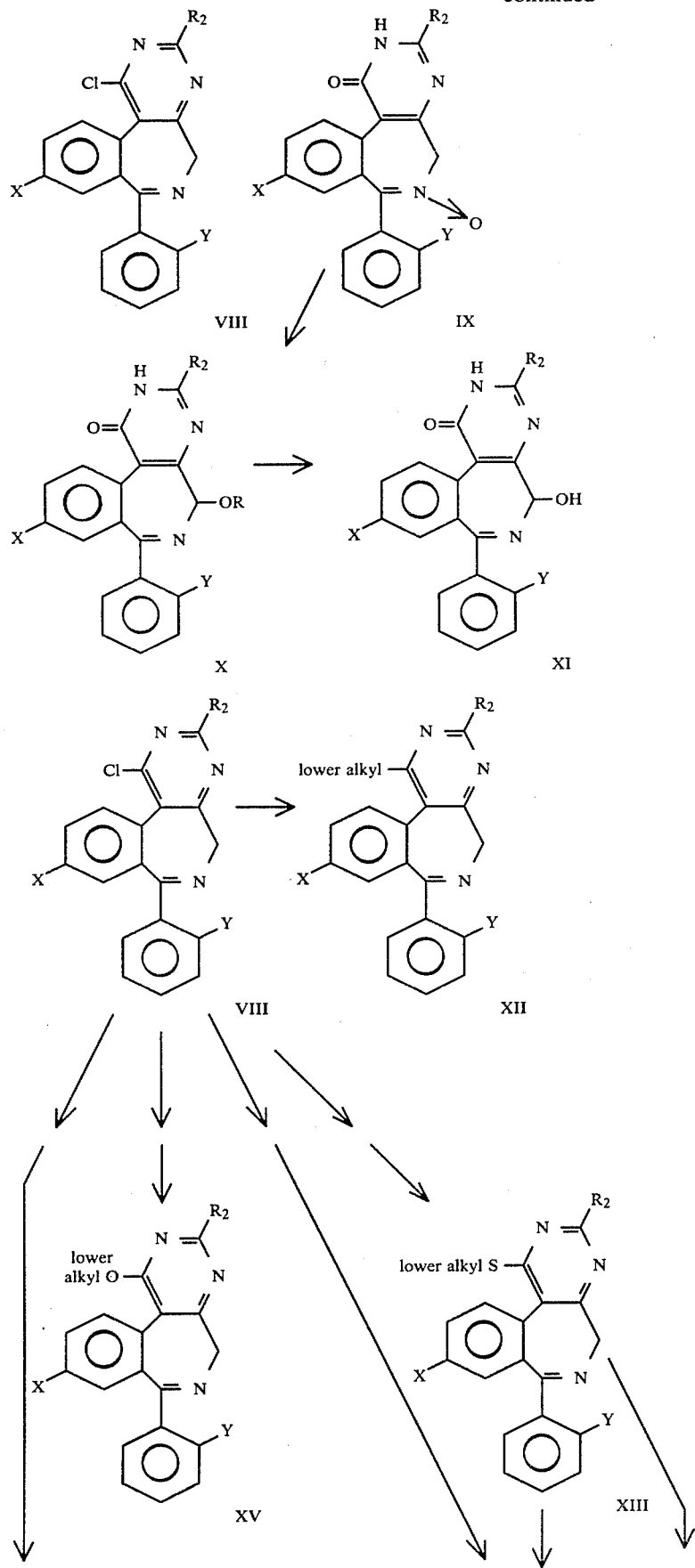

-continued

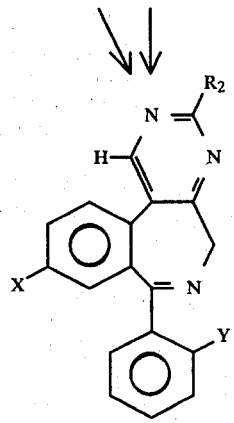

XVI

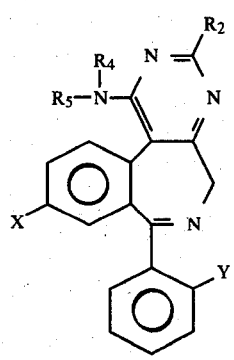

XIV wherein R₂, R₃, X and Y are as above and R is acyl.

III→IV+V

The compound of formula III is a known material having been disclosed in U.S. patent application Ser. No. 150,508 together with a method for its preparation.

The compound of formula III is reacted with carbon monoxide in the presence of a $C_1$ to $C_6$ alcohol, a tertiary amine, e.g., triethylamine or tri-n-butyl amine, a palladium catalyst, such as, palladium acetate or palladium bromide and triphenylphosphine or dibromobis(-triphenylphosphine) palladium II and optionally cuprous iodide or hydrazine. The reaction temperature may vary from about 60° C. to 120° C. with preferably about 100° C. The reaction may or may not be run under pressure in order to shorten the reaction time.

IV+V→VI

The compounds of formulas IV and V are reacted with an amidine, such as, formamidine, acetamidine or guanidine in the presence of a base, such as, an alkali metal alkoxide, e.g., sodium or potassium methoxide, ethoxide or butoxide. Suitable solvents include $C_1$ to $C_4$ alcohols. The reaction temperature may range from about room temperature to reflux with the preferred temperature dependent on the amidine chosen but not to exceed about 100° C.

VI→VII

The compound of formula VI is reacted with an oxidizing agent, such as, manganese dioxide in a suitable solvent, e.g., methylene chloride, tetrahydrofuran, or dimethylformamide. The reaction temperature may vary from about room temperature to 100° C. with about 60° C. as preferred.

The oxo compound of formula VII is a tautomeric form of the corresponding compound of formula I wherein $R_1$ is hydroxy. The same is true for the compounds of formulas X and XI and similarly the oxo compound of formula IX is a tautomeric form of the 6-oxide of the corresponding compound of formula I wherein $R_1$ is hydroxy.

VII→IX

The compound of formula VI is reacted with a peracid, such as, m-chloroperbenzoic or pertrifluoroacetic acid in a halogenated hydrocarbon solvent such as methylene chloride. The reaction temperature may vary from about −20° C. to room temperature with about 0° C. as preferred.

IX→X

The compound of formula VIII is reacted with an acid anhydride derived from $C_1$ to $C_6$ carboxylic acids, such as, acetic, propionic, etc. or trifluoroacetic anhydride. The reaction temperature may vary from about 40° C. to reflux temperature with about reflux temperature as preferred. The reaction temperature however should not exceed 125° C.

X→XI

The compound of formula X is reacted with an aqueous alkali metal carbonate, such as, sodium or potassium carbonate or an aqueous alkali metal hydroxide, such as, sodium or potassium hydroxide. A co-solvent may be utilized, such as, a $C_1$ to $C_6$ alcohol or tetrahydrofuran. The reaction temperature may be varied from about 0° C. to 100° C., preferably from about room temperature to 100° C.

VII→VIII

The compound of formula VII is reacted with a phosphoryl halide, e.g., a chloride or bromide. A co-solvent, such as, a chlorinated hydrocarbon, e.g., methylene chloride or chloroform may be also utilized. The reaction temperature may be varied from about room temperature to reflux of the selected solvent. About room temperature is preferred.

VIII→XII

The compound of formula VIII or the corresponding 1-bromo compound is reacted with an organo metallic reagent, such as, a lower alkyl lithium or a lower alkyl cuprate in an ether solvent, such as, diethyl ether or tetrahydrofuran. The reaction temperature may be varied from about −78° C. to 0° C. with about −78° C. as preferred.

VIII→XIII

The compound of formula VIII or the corresponding 1-bromo compound is reacted with an alkali metal salt of a lower alkyl mercaptan in a polar solvent, such as, dimethylformamide or dimethyl sulfoxide. The reaction temperature may be varied from about −78° C. to room temperature with about room temperature as preferred.

VIII→XIV and XIII→XIV

The compound of formula VIII or the corresponding 1-bromo compound is reacted with ammonia or a primary or secondary amine in a polar solvent, such as, dimethylformamide or dimethyl sulfoxide. The reaction temperature may be varied from about room temperature to 100° C. with about 60° C. as preferred. Similarly a compound of formula XIII can be used as starting material for producing a compound of formula XIV.

VIII→XV

The compound of formula VIII or the corresponding 1-bromo compound is reacted with an alkali metal alkoxide in the corresponding $C_1$ to $C_6$ alcohol. A co-solvent, such as, an ether, e.g., tetrahydrofuran, dioxane, etc. or dimethylformamide may also be utilized. The reaction temperature may vary from about 0° C. to room temperature with about 0° C. as preferred.

The compound of formula VIII or the corresponding 1-bromo compound may be reacted following the steps set forth in formulas VII to IX in order to produce the N-oxides of the chloro or bromo compound and that compound may thereafter be reacted to form analogous compounds to those of X and XI. Thereafter these analogous compounds may undergo the further reactions set forth in Scheme 1 wherein various $R_1$ substituents are thereafter substituted by replacement of the chloro or bromo substituent specifically described in steps VIII→XII; VIII→XIII; VIII→XVI; VIII→XV and VIII→XIV. Furthermore, compounds of formulas XII, XIV, XV and XVI can be reacted in analogy to step VII→IX and similarly 6 oxides of compounds of formulas steps IX→X and X→XI to form analogous compounds to those of formulas X and XI.

VIII→XVI

A compound of the formula VIII or the corresponding 1-bromo compound is reacted with a reducing agent, such as, hydrogen, at atmospheric pressure using Raney nickel as catalyst in a $C_1$ to $C_4$ alcohol or zinc and ammonium chloride in a mixture of water and tetrahydrofuran or water and dioxane. The reaction temperature varies from 0° C. to the reflux temperature of the solvent chosen with room temperature preferred.

XIII→XVI

A compound of the formula XVII is reacted with Raney nickel in a $C_1$ to $C_4$ alcohol. The reaction temperature varies from 0° C. to the reflux temperature of the chosen solvent with about reflux temperature preferred. This reaction constitutes a desulfurization which is a well-known process in the art.

The expression "pharmaceutically acceptable salts" is used to include salts with both inorganic and organic pharmaceutically acceptable strong acids, such as, sulfuric acid, hydrochloric acid, nitric acid, methanesulfonic acid and p-toluenesulfonic acid. Such salts can be formed quite readily by those skilled in the art with the prior art and the nature of the compound to be placed in salt form in view.

The pyrimido[4,5-d][2]benzazepines above are useful as pharmaceuticals and are characterized by activity as sedatives and anxiolytic agents. These compounds can be used in the form of conventional pharmaceutical preparations; for example, the aforesaid compounds can be mixed with conventional organic or inorganic, inert pharmaceutical carriers suitable for parenteral or enteral administration such as for example, water gelatin, lactose, starch, magnesium stearate, talc, vegetable oil, gums, polyalkylene glycols, Vaseline or the like. They can be administered in conventional pharmaceutical forms, e.g., solid forms, for example, tablets, dragees, capsules, suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservatives, stabilizing agents, wetting agents, emulsifying agents, salts for the adjustment of osmotic pressure, or buffers. The compositions can also contain other therapeutically active materials.

A suitable pharmaceutical dosage unit can contain from about 1 to about 500 mg of the benzazepine end products with a dosage range of from about 1 mg to about 100 mg being the preferred oral administration and a dosage range of from about 1 mg to about 50 mg being preferred for parenteral administration. However, for any particular subject, the specific dosage regimen should be adjusted according to individual need and the professional judgment of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subject each containing a predetermined quantity of active material calculated to produce the desired therapeutic effect in association with the required pharmaceutical diluent, carrier or vehicle.

Preferred compounds of formula I are those wherein $R_1$ is as above, $R_3$ is hydrogen and $R_2$ is hydrogen or lower alkyl.

Especially preferred compounds of formula I include the following:

A. 9-chloro-3-methyl-7-phenyl-5H-pyrimido[4,5-d][2]benzazepin-1(2H)-one
B. 9-chloro-7-(2-fluorophenyl)-3-methyl-5H-pyrimido[4,5-d][2]benzazepin-1(2H)-one
C. 1,9-dichloro-3-methyl-7-phenyl-5H-pyrimido[4,5-d][2]benzazepine
D. 9-chloro-1,3-dimethyl-7-phenyl-5H-pyrimido[4,5-d][2]benzazepine
E. 9-chloro-7-(2-fluorophenyl)-3-methyl-1-methoxy-5H-pyrimido[4,5-d][2]benzazepine The compound of formula III may be prepared from an iodobenzophenone appropriately substituted by X and Y. The iodobenzophenone is prepared by diazotizing the corresponding known aminobenzophenone using sodium nitrite in sulfuric acid and isolating the salts by precipitating the respective tetrafluoroborate salts which were thereafter slurried in water and treated with aqueous potassium iodide to give the iodobenzophenone. These reactions are carried out utilizing methods known in the art.

The iodobenzophenone thereafter is reacted with propargyl phthalimide in the presence of palladium chloride or acetate, cuprous iodide, an organophosphine, for example, triphenylphosphine, and a tertiary or secondary amine, such as, diethylamine or diisopropylamine. The reaction solvent may be the amine itself, e.g., diethylamine, a halogenated hydrocarbon, e.g., methylene choride, dimethylformamide or ether solvents. The reaction temperature may range from about 0° C. to about 70° C. with ambient temperatures as preferred.

The presence of cuprous iodide is mandatory if the reaction is carried out at room temperature or below while this is not the case if the reaction is carried out with heating. The presence of the organophosphine is not absolutely necessary but highly advantageous. Instead of the palladium salt plus the organophosphine an appropriate complex such as dichloro bis(triphenylphosphine)palladium II can also be utilized.

The resultant product is hydrogenated using a Lindlar catalyst (prehydrogenated 10% palladium on barium sulfate) at about atmospheric pressure and about room temperature. Solvents suitable for the reaction include $C_1$ to $C_6$ alcohols, tetrahydrofuran, dioxane or toluene.

The resultant product is thereafter reacted with an aqueous solution of a lower alkyl amine, e.g., methyl amine. A $C_1$ to $C_4$ alcohol is utilized as the solvent with ethanol as preferred. The reaction is most preferably carried out at about room temperature. The first formed open amine is not isolated but undergoes spontaneous ring closure.

The product is halogenated utilizing a halogenating agent, such as, elemental chlorine, bromine or iodine in a halogenated hydrocarbon, such as, methylene chloride or chloroform. The reaction is carried out at from about 0° C. to about room temperature with about room temperature preferred.

The product is dehydrohalogenated to produce the compound of formula III utilizing an alkali metal, e.g., potassium or sodium, hydroxide, carbonate or alkoxide. Suitable solvents include $C_1$ to $C_6$ alcohols, tetrahydrofuran, dioxane and dimethylformamide. The reaction temperature may vary from 0° C. to reflux temperature of the chosen solvent with about room temperature as preferred.

The pharmaceutical activities of the instantly claimed compounds are indicated by the pharmacological data set forth below for one of the compounds of the invention.

TESTS

| Compounds | Tests | | |
| --- | --- | --- | --- |
| | Foot-shock | Inclined Screen | Unanesthetized Cat |
| 1,9-dichloro-3-methyl-7-phenyl-5H—pyrimido-4,5-D-2-benzazepine | 10 mg/kg | 400 mg/kg | 10 mg/kg |

Toxicity ($LD_{50}$) = greater than 1000 mg/kg (PO)

A summary of the pharmacological tests which are known in the art is as follows:

Footshock

A pair of mice is confined under a one liter beaker placed on a grid which presents shock to the feet. At least 5 fighting episodes are elicited in a two-minute period. Pairs of mice are marked and pretreated 1 hour prior to a second shocking. Logarithmic dose intervals are utilized up to a maximum of 100 mg/kg. At the 100% blocking dose, 3 out of 3 pairs must be blocked from fighting.

Inclined Screen

Groups of 6 male mice are given the test drug (maximum dose of 500 mg/kg) and then are left on the inclined screen at least 4 hours for observation of paralyzing effects severe enough to cause them to slide off the screen. If activity is observed, additional doses are taken until at least two are reached at which some, but not all of the animals slide off the screen. Doses at which mice fall off the screen due to toxicity or excitation are not included in the calculation of $PD_{50}$.

Unanesthetized Cat

Cats are treated orally and observed for minimum symptoms—usually ataxia. One cat is used at a dose of 50 mg/kg. If activity is present, up to three cats/dose are used. Results are given as minimum effective dose.

The following examples are illustrative, but not limitative of this invention. All temperatures given are in degrees centigrade, unless indicated otherwise.

EXAMPLE 1

8-Chloro-1-phenyl-5H-2-benzazepine-5-carboxylic acid butyl ester and

8-Chloro-1-phenyl-3H-2-benzazepine-5-carboxylic acid butyl ester

A 12 oz Fisher-Porter pressure bottle containing 12.5 g (33.8 mmol) of 8-chloro-5-bromo-1-phenyl-3H-2-benzazepine hydrochloride, 175 mg (0.2 mmol) of dibromobis (triphenylphosphine) palladium II and 250 mg (1.3 mmol) of cuprous iodide was flushed with argon. To the pressure bottle was then added 17 mL of tri-n-butylamine and 6.2 mL of n-butanol and the mixture was heated at 110° under 40 psi of carbon monoxide for 18 hr. The reaction was cooled, diluted with ether, and washed with water. The ether solution was dried over anhydrous sodium sulfate and concentrated at reduced pressure to yield 13.0 g of a mixture of the end products as a red oil. Purification of 4.0 g of the mixture by column chromatography (silica gel, 40 g; methylene chloride, as eluent) gave the 5-H compound as a yellow oil.

Further elution with methylene chloride yielded the 3-H compound as a yellow oil.

EXAMPLE 2

8-Chloro-1-(2-fluorophenyl)-5H-2-benzazepine-5-carboxylic acid butyl ester and

8-Chloro-1-(2-fluorophenyl)-3H-2-benzazepine-5-carboxylic acid butyl ester

A 12 oz Fisher-Porter pressure bottle containing 12.8 g (33 mmol) of 8-chloro-5-bromo-1-(2-fluorophenyl)-3H-2-benzazepine hydrochloride, 175 mg (0.2 mmol) of dibromobis(triphenylphosphine) palladium II and 250 mg (1.3 mmol) of cuprous iodide was flushed with argon. To the pressure bottle was then added 17 mL of tri-n-butylamine and 6.2 mL of n-butanol and the mixture was heated at 110° under 40 psi of carbon monoxide for 18 hr. The reaction mixture was cooled, diluted with ether and washed with water. The ether solution was dried over anhydrous sodium sulfate and concentrated at reduced pressure to give a mixture of the end product as a red oil. The oil was used without further purification.

EXAMPLE 3

8-Chloro-1-(2-chlorophenyl)-5H-2-benzazepine-5-carboxylic acid butyl ester and

8-Chloro-1-(2-chlorophenyl)-3H-2-benzazepine-5-carboxylic acid butyl ester

A 3 oz Fisher-Porter pressure bottle containing 3.5 g (9.5 mmol) of 8-chloro-5-bromo-1-(2-fluorophenyl)-3H-2-benzazepine and 70 mg (0.09 mmol) of dibromobis (triphenylphosphine) palladium II was flushed with argon. To the pressure bottle was then added 1.8 mL of n-butanol and 2.6 mL of tri-n-butylamine and the mixture was heated to 100° under 40 psi of carbon monoxide for 24 hr. The mixture was cooled, diluted with ether and washed with water. The ether solution was dried over anhydrous sodium sulfate and concentrated at reduced pressure to give a mixture of the end products as a red oil. The oil was used without further purification.

EXAMPLE 4

8-Chloro-1-(2-fluorophenyl)-5H-2-benzazepine-5-carboxylic acid methyl ester and

8-Chloro-1-(2-fluorophenyl)-3H-2-benzazepine-5-carboxylic acid methyl ester

A 3 oz Fisher-Porter pressure bottle containing 2.0 g (5.1 mmol) of 8-chloro-5-bromo-1-(2-fluorophenyl)-3H-2-benzazepine hydrochloride, 50 mg (0.06 mmol) of dibromobis (triphenylphosphine) palladium II and 60 mg (0.3 mmol) of cuprous iodide was flushed with argon. To the pressure bottle was then added 2.6 mL of tri-n-butylamine and 2.0 mL of methanol and the mixture was heated to 100° under 40 psi of carbon monoxide for 18 hr. The reaction was cooled, diluted with ether and washed with water. The ether solution was dried over anhydrous sodium sulfate and concentrated at reduced pressure. Purification of the residue by column chromatography (silica gel, 30 g; eluent, methylene chloride) gave as the first product band the 3-H compound as off-white needles, mp 106°–107°.

Further, elution with 20% (v/v) of methylene chloride gave the second product band the 5H compound as pale yellow needles, mp 125°–126°.

EXAMPLE 5

9-Chloro-4a,11b-dihydro-3-methyl-7-phenyl-5H-pyrimido-[4,5-d][2]benzazepin-1(2H)-one In one portion, 11.5 mL (49 mmol) of a 4.34 M methanol solution of sodium methoxide was added to a solution of 11.0 g (31 mmol) of a mixture of 8-chloro-1-phenyl-5H-2-benzazepine-5-carboxylic acid butyl ester and 8-chloro-1-phenyl-3H-2-benzazepine-5-carboxylic acid butyl ester and 5.7 g (60 mmol) of acetamidine hydrochloride in 200 mL of ethanol. The mixture was refluxed for 18 hr, cooled and poured into 800 mL of water. The resulting precipitate was collected by filtration and washed with ether to yield a yellow solid. Recrystallization from tetrahydrofuran gave off-white prisms, mp 155°–160°.

EXAMPLE 6

9-Chloro-4a,11b-dihydro-3-methyl-7-(2-fluorophenyl)-5H-pyrimido[4,5-d][2]benzazepin-1(2H)-one In one portion 14.0 mL of a 4.34 M methanol solution of sodium methoxide was added to a solution of 14.0 g (37.7 mmol) of a mixture of 8-chloro-1-(2-fluorophenyl)-5H-2-benzazepine-5-carboxylic acid butyl ester and 8-chloro-1-(2-fluorophenyl)-3H-2-benzazepine-5-carboxylic acid butyl ester and 7.0 g (74 mmol) of acetamidine hydrochloride in 250 mL of ethanol. The mixture was refluxed for 17 hr, cooled and poured into 1 L of water. The resulting precipitate was collected by filtration and washed with ether to yield an off-white solid, mp 150°–165°.

EXAMPLE 7

9-Chloro-4a,11b-dihydro-7-phenyl-5H-pyrimido[4,5-d][2]benzazepin-1(2H)-one ⅓ molar hydrate Dropwise 9.5 mL (41 mmol) of a 4.3 M methanol solution of sodium methoxide was added to a solution of 8.0 g (22.6 mmol) of a mixture of 8-chloro-1-phenyl-5H-2-benzazepine-5-carboxylic acid butyl ester and 8-chloro-1-phenyl-3H-2-benzazepine-5-carboxylic acid butyl ester and 6.5 g (62.4 mmol) of formamidine acetate in 70 mL of ethanol. When the addition was complete stirring at room temperature was continued for 30 min. The reaction was diluted with water and extracted with methylene chloride. The methylene chloride solution was washed with water, dried over anhydrous sodium sulfate and concentrated at reduced pressure. The residue was crystallized from a mixture of ether and petroleum ether to give a yellow solid. Recrystallization from a mixture of ether and methylene chloride gave pale yellow prisms, mp 150°–155°.

The filtrate from the crystallization of the end product was concentrated at reduced pressure. The residue was purified by plug filtration (silica gel, eluent methylene chloride) to give the 5-H starting material as a yellow oil, whose TLC $R_f$ value was identical to an authentic sample.

EXAMPLE 8

9-Chloro-3-methyl-7-phenyl-5H-pyrimido[4,5-d][2]benzazepin-1(2H)-one

A mixture of 20.0 g (230 mmol) of activated manganese dioxide and 5.3 g (14.8 mmol) of 9-chloro-4a,11b-dihydro-3-methyl-7-phenyl-5H-pyrimido[4,5-d][2]benzazepin-(2H)-one in 500 mL of tetrahydrofuran was refluxed for 2 hr. The manganese dioxide was removed by filtration through celite and the filtrate was concentrated at reduced pressure to give a pale yellow solid, mp 245°–248°. recrystallization from a mixture of methylene chloride and ether gave colorless crystals, mp 248°–249°.

EXAMPLE 9

9-Chloro-3-methyl-7-(2-fluorophenyl)-5H-pyrimido[4,5-d][2]benzazepin-1(2H)-one

The preparation of 9-chloro-3-methyl-7-(2-fluorophenyl)-5H-pyrimido[4,5-d][2]benzazepin-1(2H)-one was conducted in the same manner as the preparation of 9-chloro-3-methyl-7-phenyl-5H-pyrimido[4,5-d][2]benzazepin-1(2H)-one to give pale yellow prisms, mp 262°–264°.

EXAMPLE 10

9-Chloro-3-methyl-7-(2-chlorophenyl)-5H-pyrimido[4,5-d][2]benzazepin-1(2H)-one

In one portion 6.0 mL (24 mmol) of a 4.0 M methanol solution of sodium methoxide was added to 4.35 g (11.2 mmol) of a mixture of 8-chloro-1-(2-chlorophenyl)-5H-2-benzazepine-5-carboxylic acid butyl ester and 8-chloro-1-(2-chlorophenyl)-3H-2-benzazepine-5-carboxylic acid butyl ester and 2.5 g (26 mmol) of acetamidine hydrochloride in 50 mL of ethanol. The mixture was refluxed for 6 hr and diluted with water. The resulting precipitate was collected by filtration and washed with ether to give an amorphous tan solid.

A mixture of the tan solid and 6.0 g of activated manganese dioxide in 100 mL of tetrahydrofuran was refluxed for 4 hr. The manganese dioxide was removed by filtration over celite and the filtrate was concentrated at reduced pressure to give a cream colored solid. Recrystallization from ethyl acetate gave colorless crystals mp 277°–279°.

EXAMPLE 11

9-Chloro-7-phenyl-5H-pyrimido[4,5-d][2]benzazepin-1(2H)-one

A mixture of 2.2 g (6.8 mmol) of 9-chloro-4a,11b-dihydro-7-phenyl-5H-pyrimido[4,5-d][2]benzazepin-1(2H)-one and 10 g (110 mmol) of activated manganese dioxide in 100 mL of tetrahydrofuran was refluxed for 18 hr. The mixture was cooled, the manganese dioxide was removed by filtration over celite and the filtrate was concentrated at reduced pressure. Purification of the residue by column chromatography (silica gel 10 g; eluents, 20% ether in methylene chloride followed by 50% ethyl acetate in methylene chloride) gave pale yellow prisms, mp 226°–229°.

EXAMPLE 12

3-Amino-9-chloro-7-(2-fluorophenyl)-5H-pyrimido[4,5-d][2]benzazepin-1(2H)-one

In one portion 5.0 mL (22 mmol) of a 4.34 M methanol solution of sodium methoxide was added to a mixture of 5.0 g (13.5 mmol) of a mixture of 8-chloro-1-(2-fluorophenyl)-5H-2-benzazepine-5-carboxylic acid butyl ester and 8-chloro-1-(2-fluorophenyl)-3H-2-benzazepine-5-carboxylic acid butyl ester and 5.0 g (27.7 mmol) of guanidine carbonate in 100 mL of ethanol. The mixture was refluxed for 1 hr and diluted with water. The resulting precipitate was collected by filtration and washed with ether to give a brown solid.

A mixture of the brown solid and 5.0 g of activated manganese dioxide in 175 mL of dimethylformamide was heated to 100° for 2 hr. The manganese dioxide was removed by filtration over celite and the filtrate was partitioned between a mixture of methylene chloride and water. The methylene chloride solution was dried over anhydrous sodium sulfate and concentrated at reduced pressure to give a tan solid. Recrystallization from a mixture of methanol and tetrahydrofuran gave off-white prisms, mp 331°–332°.

EXAMPLE 13

1,9-Dichloro-3-methyl-7-phenyl-5H-pyrimido[4,5-d][2]benzazepine

A solution of 3.5 g (10.4 mmol) of 9-chloro-3-methyl-7-phenyl-5H-pyrimido[4,5-d][2]benzazepin-1(2H)-one and 22 mL of phosphorous oxychloride in 100 mL of methylene chloride was stirred at room temperature for 18 hr. The reaction mixture was concentrated at reduced pressure to a solid residue. The residue was partitioned between ice cold saturated aqueous sodium bicarbonate and methylene chloride. The methylene chloride solution was dried over anhydrous sodium sulfate and concentrated at reduced pressure to a yellow residue. Purification by column chromatography (silica gel, 40.0 g; eluent:methylene chloride ether, 10:1) gave a pale yellow solid, mp 190°–192°. A portion was recrystallized from a mixture of ether and petroleum ether to yield colorless prisms, mp 191°–193°.

EXAMPLE 14

1,9-Dichloro-3-methyl-7-(2-fluorophenyl)-5H-pyrimido[4,5-d][2]benzazepine hydrochloride A mixture of 3.3 g (9.3 mmol) of 9-chloro-3-methyl-7-(2-fluorophenyl)-5H-pyrimido-[4,5-d][2]benzazepin-1(2H)-one and 20 mL of phosphorous oxychloride in 90 mL of methylene chloride was stirred at room temperature for 18 hr. The reaction was concentrated at reduced pressure and the residue partitioned between aqueous sodium bicarbonate and methylene chloride. The methylene chloride solution was dried over anhydrous sodium sulfate and concentrated at reduced pressure. Purification of the residue by column chromatography (silica gel, 40 g; eluent, 10% ether in methylene chloride) gave the free base of the end products as a yellow oil.

The hydrochloride salt was prepared by the addition of one molar equivalent of a 1.4 M methanol solution of hydrogen chloride to an ether solution of end product and was isolated by filtration. Recrystallization of the hydrochloride salt from a mixture of methylene chloride and ether gave the salt as pale yellow prisms, mp 178°–182°.

EXAMPLE 15

9-Chloro-1-methoxy-3-methyl-7-phenyl-5H-pyrimido[4,5-d][2]benzazepine

A solution of 1.0 g (2.8 mmol) of 1,9-dichloro-3-methyl-7-phenyl-5H-pyrimido[4,5-d][2]benzazepine and 1.0 mL of a 4.2 M methanol solution of sodium methoxide in 20 mL of a 1:1 mixture of methanol and tetrahydrofuran was stirred at room temperature for 1 hr. The solvent was removed at reduced pressure and the residue was triturated with water to give an off-white solid. Recrystallization from a mixture of ether and petroleum ether gave colorless prisms, mp 185°–187°.

EXAMPLE 16

9-Chloro-7-(2-fluorophenyl)-1-methoxy-3-methyl-5H-pyrimido[4,5-d][2]benzazepine The preparation of 9-chloro-7-(2-fluorophenyl)-1-methoxy-3-methyl-5H-pyrimido[4,5-d][2]benzazepine was conducted in the same manner as the preparation of 9-chloro-1-methoxy-3-methyl-7-phenyl-5H-pyrimido[4,5-d][2]benzazepine to give pale yellow prisms, mp 188°–189°.

EXAMPLE 17

9-Chloro-3-methyl-1-(methylthio)-7-phenyl-5H-pyrimido[4,5-d][2]benzazepine

In one portion 1.0 g (2.8 mmol) of 1,9-dichloro-3-methyl-7-phenyl-5H-pyrimido[4,5-d][2]benzazepine was added to a solution of 150 mg (3.1 mmol) of 50% mineral oil dispersion of sodium hydride and an excess of methyl mercaptan (>3.1 mmol) in 25 mL of dimethylformamide. The mixture was stirred at room temperature for 30 min and diluted with water. The resulting precipitate was collected by filtration to give a yellow solid. Recrystallization from a mixture of ether and methylene chloride gave pale yellow prisms, mp 181°–183°.

EXAMPLE 18

N-(9-Chloro-3-methyl-7-phenyl-5H-pyrimido[4,5-d][2]benzazepin-1-yl)-N',N'-dimethyl-1,3-propanediamine ½ molar hydrate A solution of 1.0 g (2.8 mmol) of 1,9-dichloro-3-methyl-7-phenyl-5H-pyrimido[4,5-d][2]benzazepine and 1 mL of dimethylaminopropylamine in 25 mL of dimethylformamide was heated to 65° for 16 hr. The mixture was poured into ice water and the resulting precipitate was collected by filtration to give a tan solid. Recrystallization from a mixture of ether and petroleum ether gave colorless needles, mp 124°–127°.

The hydrochloride salt was prepared by the addition of one molar equivalent of a 1.4 M methanol solution of hydrogen chloride to a methanol solution of the end product and isolated by precipitating the salt with the addition of ether. Recrystallization from a mixture of methanol and ether gave the hydrochloride salt as off-white prisms, mp 190°–194°.

EXAMPLE 19

9-Chloro-1,3-dimethyl-7-phenyl-5H-pyrimido[4,5-d][2]benzazepine ¼ molar etherate Dropwise 13.2 ml (18.5 mmol) of a 1.4 M ether solution of methyl lithium was added to a suspension of 1.7 g (8.9 mmol) of cuprous iodide in 50 mL of ether which was cooled to 0°. A solution of 0.8 g (2.2 mmol) of 1,9-dichloro-3-methyl-7-phenyl-5H-pyrimido[4,5-d][2]benzazepine in 30 mL of ether was added dropwise to the ether solution of lithium dimethylcuprate which was further cooled to −25°. The mixture was stirred at −25° for 1 hr, warmed to room temperature, diluted with water and saturated with hydrogen sulfide. The resulting precipitate was removed by filtration over celite and he filtrate was concentrated at reduced pressure. Purification of the residue by column chromatography (silica gel, 10 g; eluent, 20% ether in methylene chloride) gave an oil which was crystallized from a mixture of ether and petroleum ether to give off-white needles, mp 121°–124°.

EXAMPLE 20

1-[4-Chloro-2-benzoylphenyl]-3-phthalimidopropene

A mixture of 2.0 g of (5 mmole) of 1-[4-chloro-2-benzoylphenyl]-3-phthalimidopropyne and 0.1 g of prehydrogenated 10% palladium on barium sulfate in 50 ml of tetrahydrofuran was hydrogenated at room temperature and atmospheric pressure until 85 ml of hydrogen was absorbed. The catalyst was removed by filtration and the filtrate was concentrated at reduced pressure to dryness. The residue was crystallized from ether to give a white solid, mp 70°–72° C. Recrystallization from ether gave colorless prisms, mp 70°–72° C.

EXAMPLE 21

8-Chloro-1-phenyl-3H-2-benzazepine hydrochloride

A mixture of 6 g (15 mmole) of 1-[4-chloro-2-benzoylphenyl]-3-phthalimidopropene, 0.9 g (18 mmole) of 85% hydrazine hydrate and 70 ml of 95% ethanol was refluxed for 2.5 hr. The insoluble precipitate formed was separated by filtration. The filtrate was acidified with ice cold dilute hydrochloric acid and extracted with ether. The aqueous layer was separated, made alkaline with dilute sodium hydroxide and extracted with methylene chloride. The methylene chloride solution was dried over anhydrous sodium sulfate, acidified with methanolic hydrogen chloride, diluted with isopropanol and concentrated at reduced pressure to a small volume. The crude product was collected by filtration to give tan prisms, mp 223°–225° C. dec.

EXAMPLE 22

9-Chloro-3-methyl-7-phenyl-5H-pyrimido[4,5-d][2]benzazepin-1(2H)-one 6-oxide A solution of 2.8 g (8.3 mmol) of 9-chloro-3-methyl-7-phenyl-5H-pyrimido[4,5-d][2]benzazepin-1(2H)-one and 2.5 g (11.5 mmol) of 85% m-chloroperbenzoic acid in 110 mL of methylene chloride was stirred at room temperature for 2.5 hr. The reaction mixture was washed with saturated aqueous sodium bicarbonate, dried over anhydrous sodium sulfate and concentrated at reduced pressure to give a yellow solid. Recrystallization from methanol gave pale yellow prisms, mp 219°–221°.

EXAMPLE 23

5-(Acetyloxy)-9-chloro-3-methyl-7-phenyl-5H-pyrimido[4,5-d][2]benzazepin-1(2H)-one A mixture of 0.5 g (1.4 mmol) of 9-chloro-3-methyl-7-phenyl-5H-pyrimido[4,5-d][2]benzazepin-1(2H)-one 6-oxide and 10 mL of acetic anhydride was heated on a steam bath for 3 hr. The reaction mixture was concentrated at reduced pressure and the crystalline product separated. Recrystallization from methylene chloride gave the product as cream colored crystals, mp >320°.

was collected by filtration to give an off-white solid. Recrystallization from tetrahydrofuran gave the product as colorless crystals, mp 253°-255° (dec.).

EXAMPLE 25

TABLET FORMULATION (Direct compression)

| Item | Ingredients | mg/tablet | mg/tablet | mg/tablet | mg/tablet |
|------|-------------|-----------|-----------|-----------|-----------|
| 1. | 9-chloro-7-(2-fluorophenyl)-3-methyl-5H—pyrimido[4,5-d][2]benzazepin-1(2H)—one 1,9-dichloro-3-methyl-7-phenyl-5H—pyrimido[4,5-d][2]benzazepine | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |
|    | Weight of tablet | 300 mg | 300 mg | 300 mg | 300 mg |

Procedure:
1. Mix Item 1 with an equal amount of lactose. Mix well.
2. Mix with Items 3 and 4, and the remaining amount of Item 2. Mix well.
3. Add magnesium stearate and mix for 3 minutes.
4. Compress on a suitable press equipped with appropriate punches.

EXAMPLE 26

TABLET FORMULATION (Wet granulation)

| Item | Ingredients | mg/tablet | mg/tablet | mg/tablet | mg/tablet |
|------|-------------|-----------|-----------|-----------|-----------|
| 1. | 9-chloro-7-(2-fluorophenyl)-3-methyl-5H—pyrimido[4,5-d][2]benzazepin-1(2H)—one 1,9-dichloro-3-methyl-7-phenyl-5H—pyrimido[4,5-d][2]benzazepine | 1 | 5 | 10 | 25 |
| 2. | Lactose | 202 | 232 | 261 | 280 |
| 3. | Modified Starch | 25 | 35 | 45 | 55 |
| 4. | Pregelatinized Starch | 20 | 25 | 30 | 35 |
| 5. | Distilled Water q.s. | — | — | — | — |
| 6. | Magnesium Stearate | 2 | 3 | 4 | 5 |
|    | Weight of tablet | 250 mg | 300 mg | 350 mg | 400 mg |

Procedure:
1. Mix items 1-4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 27

CAPSULE FORMULATION

| Item | Ingredients | mg/tablet | mg/tablet | mg/tablet | mg/tablet |
|------|-------------|-----------|-----------|-----------|-----------|
| 1. | 9-chloro-7-(2-fluorophenyl)-3-methyl-5H—pyrimido[4,5-d][2]benzazepin-1(2H)—one 1,9-dichloro-3-methyl-7-phenyl-5H—pyrimido[4,5-d][2]benzazepine | 1 | 5 | 10 | 25 |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Aerosol OT | 1 | 1.5 | 2 | 2.5 |
|    | Capsule fill weight | 250 mg | 350 mg | 400 mg | 450 mg |

Procedure:
1. Mill Items 1, 2, 3 and 5 in a suitable mixer. Mill.
2. Add talc and mix well.
3. Encapsulate on suitable equipment.

EXAMPLE 24

9-Chloro-5-hydroxy-3-methyl-7-phenyl-5H-pyrimido[4,5-d][2]benzazepin-1(2H)-one

A mixture of 2.1 g (5.3 mmol) of 5-(acetyloxy)-9-chloro-3-methyl-7-phenyl-5H-pyrimido[4,5-d][2]benzazepin-1(2H)-one and 50 mL of 3 N sodium hydroxide was heated on a steam bath for 5 min. The reaction mixture was diluted with 200 mL of ice water and 50 mL of ether. The sodium hydroxide was neutralized with acetic acid and the resulting mixture stirred at room temperature for 30 min. The resulting precipitate

EXAMPLE 28

8-Chloro-1-(2-chlorophenyl)-3H-2-benzazepine

A mixture of 4.6 g (15 mmole) of 3-amino-1-[2-(2-chlorobenzoyl)-4-chlorophenyl]-propyne and 0.1 g of prehydrogenated palladium on barium sulfate in 30 ml of tetrahydrofuran was hydrogenated at room temperature and atmospheric pressure until 355 ml of hydrogen was absorbed. The catalyst was removed by filtration and the filtrate concentrated at reduced pressure. The residue was crystallized from ether to give a cream colored solid, mp 113°–115° C. Recrystallization from ether gave cream colored prisms, mp 117°–118° C.

The methanesulfonate salt of 8-chloro-1-(2-chlorophenyl)-3H-2-benzazepine was prepared by the addition of an excess of a 1 M methanol solution of methanesulfonic acid to a methanol solution of the above compound and isolated by precipitating the salt with the addition of ether. Recrystallization from a mixture of methanol and ether gave the methanesulfonate salt as colorless plates, mp 201°–202° C.

EXAMPLE 29

8-Chloro-1-(2-fluorophenyl)-3H-2-benzazepine hydrochloride

The preparation of 8-chloro-1-(2-fluorophenyl)-3H-2-benzazepine hydrochloride was conducted in the same manner as the preparation of 8-chloro-1-(2-chlorophenyl)-3H-2-benzazepine. The hydrochloride was obtained as off-white prisms, mp 210°–212° C. dec.

EXAMPLE 30

8-Chloro-4,5-dibromo-4,5-dihydro-1-phenyl-3H-2-benzazepine

Dropwise 200 ml (0.18 mole) of a 5% bromine solution in methylene chloride was added to 26.5 g (0.1 mole) of 8-chloro-1-phenyl-3H-2-benzazepine in 300 ml of methylene chloride. The mixture was stirred at room temperature for 1 hr, diluted with an excess of saturated aqueous sodium carbonate and stirred at room temperature for 15 min. The methylene chloride solution was separated, dried over anhydrous sodium sulfate, and diluted with an excess of methanolic hydrogen chloride. The acid solution was concentrated to a small volume at reduced pressure and the salt was precipitated by the addition of ether to give the salt as a colorless solid, mp 164°–165° C. Recrystallization from methylene chloride gave colorless crystals, mp 164°–165° C. dec. The compound has been found to have a second melting point of 172°–173° C. dec.

A methanol solution of the salt was neutralized with dilute aqueous sodium hydroxide and the resulting crystals collected by filtration. Recrystallization from methanol gave the end product as colorless prisms, mp 113°–115° C.

EXAMPLE 31

8-Chloro-4,5-dibromo-4,5-dihydro-1-(2-fluorophenyl)-3H-2-benzazepine

The preparation of 8-chloro-4,5-dibromo-4,5-dihydro-1-(2-fluorophenyl)-3H-2-benzazepine was conducted in the same manner as the preparation of 8-chloro-4,5-dibromo-4,5-dihydro-1-phenyl-3H-2-benzazepine to give the hydrochloride salt as a colorless solid, mp 158°–159° C. dec. and the end product as colorless prisms, mp 102°–103° C.

EXAMPLE 32

8-Chloro-4,5-dibromo-4,5-dihydro-1-(2-chlorophenyl)-3H-2-benzazepine

The preparation of 8-chloro-4,5-dibromo-4,5-dihydro-1-(2-chlorophenyl)-3H-2-benzazepine was conducted in the same manner as the preparation of 8-chloro-4,5-dibromo-4,5-dihydro-1-phenyl-3H-2-benzazepine to give pale yellow prisms, mp 139° C. dec.

EXAMPLE 33

8-Chloro-5-bromo-1-phenyl-3H-2-benzazepine hydrochloride and

8-Chloro-3-methoxy-1-phenyl-3H-2-benzazepine methanesulfonate

A solution of 24 g (53 mmole) of 8-chloro-4,5-dibromo-4,5-dihydro-1-phenyl-3H-2-benzazepine hydrochloride in 1 L of methanol and 180 ml of 10% aqueous sodium hydroxide was stirred at room temperature for 45 hr. The mixture was concentrated in vacuo to a small volume and the residue was extracted with methylene chloride. The methylene chloride solution was dried over anhydrous sodium sulfate, diluted with an excess of methanolic hydrogen chloride and concentrated in vacuo to dryness. The residue crystallized from a mixture of isopropanol and ether to give an off-white solid, mp 229°–230° C. Recrystallization from methylene chloride gave the hydrochloride of the bromo compound as colorless prisms, mp 230°–235° C. dec.

The crude mother liquors were basified with dilute aqueous sodium hydroxide and extracted with methylene chloride. The methylene chloride solution was dried over anhydrous sodium sulfate and concentrated in vacuo. Purification by column chromatography (silica gel; eluents methylene chloride, then ether) gave after concentration of the ether fractions a colorless oil. The oil was dissolved in a methanol solutio of methanesulfonic acid and the salt was precipitated by the addition of ether. Recrystallization from a mixture of methanol and ether gave off-white prisms, mp 139°–140° C.

EXAMPLE 34

8-Chloro-5-bromo-1-(2-fluorophenyl)-3H-2-benzazepine hydrochloride

A mixture of 21 g (45 mmole) of 8-chloro-4,5-dibromo-4,5-dihydro-1-(2-fluorophenyl)-3H-2-benzazepine hydrochloride, 40 ml of dioxane, 360 ml of methanol and 40 ml of 10% aqueous sodium hydroxide was stirred at room temperature for 5 hr and then concentrated at reduced pressure to a small volume. The concentrate was diluted with water and extracted with methylene chloride. The methylene chloride solution was dried over anhydrous sodium sulfate, diluted with isopropanol and an excess of methanolic hydrogen chloride. The mixture was concentrated at reduced pressure to a small volume to give the hydrochloride salt as a colorless solid, mp 231°–232° C. Recrystallization from a mixture of methylene chloride and ether gave the salt as colorless crystals, mp 233°–234° C. dec. The methanesulfonate salt of the by-product was not isolated.

EXAMPLE 35

8-Chloro-5-bromo-1-(2-chlorophenyl)-3H-2-benzazepine and

8-Chloro-3-methoxy-1-(2-chlorophenyl)-3H-2-benzazepine

A solution of 60.0 g (0.134 mole) of 8-chloro-4,5-dibromo-4,5-dihydro-1-(2-chlorophenyl)-3H-2-benzazepine and 75 ml of 40% aqueous sodium hydroxide in a mixture of 300 ml of dioxane and 900 ml of methanol was stirred at room temperature for 4 hr. The mixture was concentrated in vacuo to a small volume and the residue was extracted with methylene chloride. The methylene chloride solution was dried over anhydrous sodium sulfate, diluted with an excess of methanolic hydrogen chloride and isopropanol and concentrated in vacuo to dryness. The residue crystallized from a mixture of isopropanol and ether to give a white solid. The white solid was partitioned between methylene chloride and aqueous sodium bicarbonate. The methylene chloride solution was dried over anhydrous sodium sulfate and concentrated at reduced pressure to give an amber oil. Purification by column chromatography (silica gel, 250 g; eluent, methylene chloride) gave the bromo compound as colorless prisms, mp 125°–127° C.

The crude mother liquors were partitioned between methylene chloride and aqueous ammonium hydroxide. The methylene chloride solution was dried over anhydrous sodium sulfate and concentrated at reduced pressure. Trituration with a mixture of ether and petroleum ether gave the methoxy compound as a tan solid. Recrystallization from a mixture of ether and pertroleum ether gave cream colored prisms, mp 83°–85° C.

EXAMPLE 36

5-Chloro-2-iodobenzophenone

A mixture of 76 g (1.1 mole) of sodium nitrite and 450 ml of sulfuric acid was heated on a steam bath to ca 80° until complete solution was achieved. The solution was cooled to 30° and 232 g (1.0 mole) of 2-amino-5-chlorobenzophenone was added in portions keeping the temperature between 30° and 40°. The mixture was stirred for 1 hr and then slowly poured into 3 L of an ice and water mixture. The solution was filtered through Hy-Flo and to the stirred filtrate was added slowly a solution of 200 g (1.83 mole) of sodium fluoborate in 800 ml of water. The resulting parcipitate was collected by filtration and washed with water (2×100 ml) to give a moist white solid.

The moist 2-benzoyl-4-chlorobenzenediazonium fluoborate was slurried in 3 L of water, and a solution of 332 g (2 moles) of potassium iodide in 1 L of water was added dropwise. The mixture was stirred at room temperature for 4 hr and the resulting precipitate was collected by filtration. The crude product was added to 1 L of boiling ether, filtered, and dried with anhydrous sodium sulfate. The ether solution was concentrated to 500 ml and the addition of 100 ml of petroleum ether gave end product. A small amount of end product was recrystallized from a mixture of ether and petroleum ether to give light yellow prisms, mp 80°–82°.

EXAMPLE 37

5-Chloro-2'-fluoro-2-iodobenzophenone

The preparation of 5-chloro-2'-fluoro-2-iodobenzophenone was conducted in the same manner as the preparation of 5-chloro-2-iodobenzophenone to give the end product as light yellow prisms, mp 78°–81°.

EXAMPLE 38

2',5-Dichloro-2-iodobenzophenone

The preparation of 2'-5-dichloro-2-iodobenzophenone was conducted in the same manner as the preparation of 5-chloro-2-iodobenzophenone to give the end product as light yellow prisms, mp 64°–66°.

EXAMPLE 39

1-[4-Chloro-2-benzoylphenyl]-3-phthalimidopropyne

A mixture of 0.71 g (4.0 mmole) of palladium chloride, 2.1 g (8.0 mmole) of triphenylphosphine, 0.80 g (4.2 mmole) of cuprous iodide, 68.8 g (0.20 mole) of 5-chloro-2-iodobenzophenone, 200 ml of diethylamine, and 400 ml of methylene chloride was stirred at room temperature under argon until complete solution was obtained. In one portion, 40.0 g (0.22 mole) of N-propargylphthalimide was added to the solution and the resulting mixture stirred for 20 hr. The volatiles were removed at reduced pressure and the residue was triturated with 200 ml of isopropanol. The resulting percipitate was collected by filtration to give crude end product. Recrystallization from acetone gave cream colored prisms, mp 148°–150° C.

EXAMPLE 40

1-[4-Chloro-2-(2-fluorobenzoyl)phenyl]-3-phthalimidopropyne

The preparation of 1-[4-chloro-2-(2-fluorobenzoyl)-phenyl]-3-phthalimidopyropyne was conducted in a similar manner as the preparation of 1-[4-chloro-2-benzoylphenyl]-3-phthalimidopropyne to give cream colored prisms, mp 158°–161° C.

EXAMPLE 41

1-[4-Chloro-2-(2-chlorobenzoyl)phenyl]-3-phthalimidopropyne

The preparation of 1-[4-chloro-2-(2-chlorobenzoyl)-phenyl]-3-phthalimidopropyne was conducted in the same manner as the preparation of 1-[4-chloro-2-benzoylphenyl]-3-phthalimidopropyne to give cream colored prisms, mp 144°–145° C.

EXAMPLE 42

3-Amino-1-[4-chloro-2-(2-fluorobenzoyl)phenyl]-propyne

Method A

A mixture of 50 g of 1-[4-chloro-2-(2-fluorobenzoyl)-phenyl]-3-phthalimidopropyne, 50 ml of 40% aqueous methylamine and 150 ml of dimethylformamide was stirred at room temperature for 25 min. Dropwise 500 ml of water was added, and the resulting precipitate was collected by filtration. The precipitate was dissolved in methylene chloride dried over anhydrous sodium sulfate, and concentrated at reduced pressure to give a pale yellow solid. Recrystallization from ether gave pale yellow prisms, mp 89°–91° C.

Method B

A mixture of 400 g (0.96 mole) of 1-[4-chloro-2-(2-fluorobenzoyl)phenyl]-3-phthalimidopropyne, 1.3 L of ethanol and 300 ml of 40% aqueous methylamine was stirred at room temperature for 2 hr. Dropwise 2.8 l of water was added, and the resulting precipitate was collected by filtration to give a pale yellow solid, mp 70°–80° C. Recrystallization from ether gave pale yellow prisms, mp 80°–91° C.

EXAMPLE 43

3-Amino-1-[4-chloro-2-(2-chlorobenzoyl)phenyl]-propyne

The preparation of 3-amino-1-[4-chloro-2-(2-chlorobenzoyl)phenyl]propyne was conducted in the same manner as the preparation of 3-amino-1-[4-chloro-2-(2-fluorbenzoyl)phenyl]propyne to give pale yellow prisms, mp 81°–82° C.

What is claimed:

1. A compound of the formula

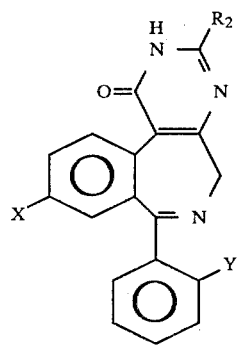

wherein $R_2$ is selected from the group consisting of hydrogen, lower alkyl and amino, X is halogen and Y is hydrogen or halogen.

2. A compound of the formula

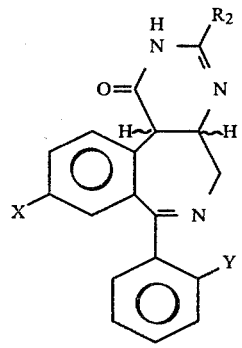

wherein $R_2$ is selected from the group consisting of hydrogen, lower alkyl and amino; X is halogen and Y is hydrogen or halogen.

3. A compound of the formula

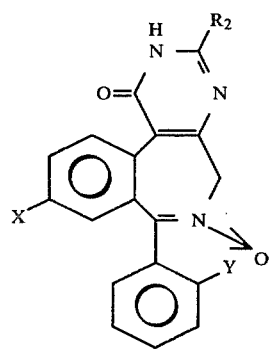

wherein $R_2$ is selected from the group consisting of hydrogen, lower alkyl and amino; X is halogen and Y is hydrogen or halogen.

4. The compound: 9-Chloro-3-methyl-7-phenyl-5H-pyrimido[4,5-d][2]benzazepin-1(2H)-one.

5. The compound: 9-Chloro-7-(2-fluorophenyl)-3-methyl-5H-pyrimido[4,5-d][2]benzazepin-1(2H)-one.

* * * * *